US010842459B2

(12) United States Patent
Isogai et al.

(10) Patent No.: US 10,842,459 B2
(45) Date of Patent: Nov. 24, 2020

(54) CONTROL SYSTEM AND RADIOGRAPHIC IMAGING SYSTEM

(71) Applicant: Konica Minolta, Inc., Tokyo (JP)

(72) Inventors: Kohei Isogai, Kawasaki (JP); Hidetake Tezuka, Tachikawa (JP); Nobuyuki Miyake, Yokohama (JP); Kentaro Hara, Hino (JP); Masahiro Kuwata, Machida (JP); Koji Kashima, Higashiyamato (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/448,640

(22) Filed: Jun. 21, 2019

(65) Prior Publication Data

US 2020/0008771 A1 Jan. 9, 2020

(30) Foreign Application Priority Data

Jul. 9, 2018 (JP) .................................. 2018-129641

(51) Int. Cl.
*G01N 23/04* (2018.01)
*A61B 6/00* (2006.01)
(Continued)

(52) U.S. Cl.
CPC .............. *A61B 6/54* (2013.01); *A61B 6/4208* (2013.01); *A61B 6/44* (2013.01); *A61B 6/463* (2013.01);
(Continued)

(58) Field of Classification Search
CPC ....... A61B 6/42; A61B 6/4208; A61B 6/4233; A61B 6/44; A61B 6/4405; A61B 6/463;
(Continued)

(56) References Cited

U.S. PATENT DOCUMENTS

2013/0182934 A1* 7/2013 Topfer .................... G06T 5/005
382/132
2015/0281564 A1* 10/2015 Shin .................... H04N 5/23293
715/771

(Continued)

FOREIGN PATENT DOCUMENTS

JP 2006305106 A 11/2006

*Primary Examiner* — Irakli Kiknadze
(74) *Attorney, Agent, or Firm* — Lucas & Mercanti, LLP

(57) ABSTRACT

A control system includes a radiation emission apparatus and a radiographic imaging apparatus that generates image data by receiving radiation. A first apparatus of the radiation emission apparatus and the radiographic imaging apparatus includes a first timer that performs time measurement to periodically generate first time measurement information. A second apparatus of the radiation emission apparatus and the radiographic imaging apparatus includes a second timer that performs time measurement to periodically generate second time measurement information. The first apparatus includes an interface that transmits the first time measurement information to the second timer. At least one apparatus includes a hardware processor which adjusts the operation of the first or second timer based on adjustment conditions in a state where the second timer does not acquire the first time measurement information.

11 Claims, 13 Drawing Sheets

(51) Int. Cl.
  *H05G 1/38*    (2006.01)
  *G01T 7/00*    (2006.01)
  *G03B 42/02*   (2006.01)
  *G01T 1/17*    (2006.01)

(52) U.S. Cl.
  CPC ............... *G01T 1/17* (2013.01); *G01T 7/00* (2013.01); *G03B 42/02* (2013.01); *H05G 1/38* (2013.01)

(58) Field of Classification Search
  CPC .. A61B 6/486; A61B 6/54; A61B 6/56; A61B 3/0025; A61B 3/0033; A61B 3/0058; A61B 3/14; A61B 3/18; A61B 6/4494; A61B 6/542; A61B 6/566; A61B 6/4283; G01T 1/1663; G01T 1/17; G01T 7/00; H05G 1/38; G06N 3/02; G06N 20/00; G06N 3/006; G06N 3/0445; G06N 3/0454; G06N 3/0472; G06N 3/084; G06N 3/088; G06N 3/126; G06N 5/046; G06N 7/005; G06N 20/10; G06N 20/20; G06N 3/0427; G06N 3/0436
  USPC ........................................................ 378/62
  See application file for complete search history.

(56) References Cited

U.S. PATENT DOCUMENTS

2017/0258454 A1\* 9/2017 Lerch ................... A61B 8/5238
2018/0116625 A1\* 5/2018 Kim ..................... G01R 31/3842

\* cited by examiner

| 7 OCTETS | 1 | 6 | 6 | 2 | 46 - 1500 | 4 |
|---|---|---|---|---|---|---|
| PREAMBLE | SFD | DESTINATION ADDRESS | TRANSMISSION SOURCE ADDRESS | LENGTH / TYPE | DATA / LLC | FCS |

US 10,842,459 B2

CONTROL SYSTEM AND RADIOGRAPHIC IMAGING SYSTEM

BACKGROUND

1. Technological Field

The present invention relates to a control system and a radiographic imaging system including the system.

2. Description of the Related Art

In order to perform imaging with an imaging apparatus, it is necessary to match the timing of radiation emission by a control device with the timing of charge accumulation and readout by the imaging apparatus. In particular, in moving image capturing in which pulsed radiation emission is repeated to generate a plurality of frame images, the shorter the interval between frames, the shorter the accumulation period of the imaging apparatus. Accordingly, highly accurate control (depending on circumstances, on the order of several ms to several hundreds of μs) of the timing of radiation emission and the timing of charge accumulation and readout is required.

The control of timing is generally performed by exchanging timing information between the imaging apparatus and the control device. If the communication between the control device and the imaging apparatus is wired communication using a dedicated line, there is an advantage that highly accurate timing control is possible. However, when the imaging apparatus is directly inserted under a patient for imaging, there is a disadvantage that it is difficult to perform imaging since the handling of the imaging apparatus is poor.

Therefore, it is required to make the imaging apparatus wireless. However, in a case where a method of communication between the control device and the imaging apparatus is a best effort type access method (CSMA/CA or the like), such as a WLAN, the adjustment time of packet transmission is indefinite. For this reason, since the communication delay varies, there is a problem in realizing highly accurate timing control.

In order to cope with such a problem, for example, a technique described in JP 2006-305106 A has been proposed. Specifically, first, an imaging apparatus is connected to a control device by wire, and the control device and the imaging apparatus share radiation imaging available period information. Then, after the radiation imaging available period information is shared, the imaging apparatus and the control device independently determine whether or not this is a radiation imaging available period using a timer built in each of the imaging apparatus and the control device. In a case where an X-ray exposure request signal is asserted within the radiation imaging available period, imaging is performed. In a case where the X-ray exposure request signal is asserted when this is not the radiation imaging available period, the imaging apparatus and the control device provide cancellation notification or wait until the next radiation imaging available period comes.

In the case of the technique described in JP 2006-305106 A, however, one exposure is performed per one X-ray generator exposure request switch (hereinafter, referred to as an exposure request SW). Therefore, it is necessary to operate or control the exposure request SW each time the exposure is performed. In addition, since the exposure request SW has a two-step configuration of 1st SW and 2nd SW and the exposure is performed first by operating the 2nd SW after the operation of the 1st SW, a predetermined amount of time is required for one exposure. That is, when moving image capturing is performed using the technique described in JP 2006-305106 A, the frame rate becomes very low and accordingly, there is a high possibility that a good moving image cannot be acquired.

In addition, due to the influence of error in the frequency of an oscillator provided in each of the control device and the imaging apparatus and the like, a slight difference often occurs between the operating speed of the control device and the operating speed of the imaging apparatus. For this reason, even if the control device and the imaging apparatus described in JP 2006-305106 A are used, in imaging for a relatively long time, such as moving image capturing, there is a possibility that the start timing of the radiation imaging available period information shared by the control device and the imaging apparatus will be shifted. In particular, in the case of the technique described in JP 2006-305106 A, as described above, when the X-ray exposure request signal is asserted outside the radiation imaging available period, the imaging apparatus and the control device provide cancellation notification or wait until the next radiation imaging available period comes. Therefore, since the exposure is not performed at fixed intervals, there is a possibility that a good moving image cannot be acquired.

SUMMARY

An object of the invention is to make it possible to stably perform moving image capturing even if time measurement information is not transmitted from one apparatus to the other apparatus in a radiographic imaging system including a radiation emission apparatus that emits radiation and a radiographic imaging apparatus that generates image data by receiving radiation.

To achieve at least one of the abovementioned objects, according to an aspect of the present invention, a control system includes:

a radiation emission apparatus that generates radiation; and a radiographic imaging apparatus that generates image data by receiving radiation, wherein a first apparatus of the radiation emission apparatus and the radiographic imaging apparatus includes a first timer that performs time measurement in conjunction with the first apparatus to periodically generate first time measurement information, a second apparatus of the radiation emission apparatus and the radiographic imaging apparatus includes a second timer that performs time measurement in conjunction with the second apparatus to periodically generate second time measurement information, the first apparatus includes an interface that transmits the first time measurement information generated by the first timer to the second timer of the second apparatus, and at least one apparatus of the radiation emission apparatus and the radiographic imaging apparatus includes:

a storage that stores adjustment conditions for adjusting an operation of the first or second timer provided in the at least one apparatus; and a hardware processor that adjusts the operation of the first or second timer provided in the at least one apparatus based on the stored adjustment conditions in a state where the second timer does not acquire the first time measurement information.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIGS. 21A, 21B, 21C, and 20D are diagrams illustrating examples of a signal that a radiographic imaging system according to Example 12 of the same embodiment uses for communication.

DETAILED DESCRIPTION OF EMBODIMENTS

Hereinafter, one or more embodiments of the present invention will be described with reference to the drawings. However, the scope of the invention is not limited to the disclosed embodiments.

Radiographic Imaging System

Figure 1:
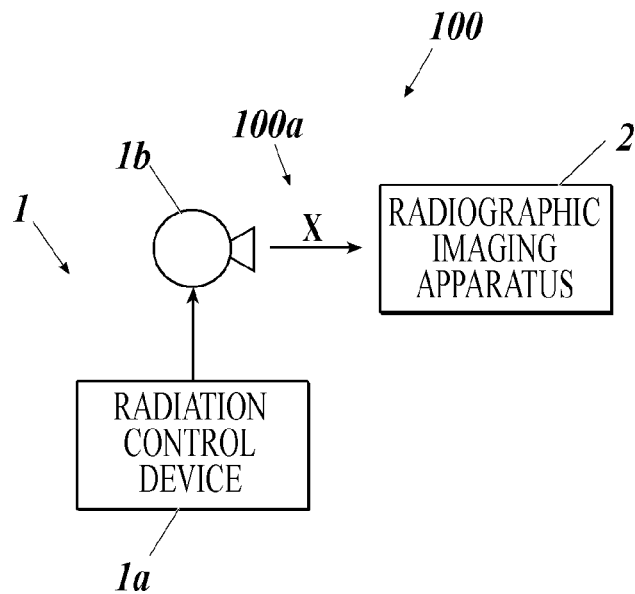
FIG. 1 is a block diagram illustrating the configuration of a radiographic imaging system according to an embodiment of the invention.

First, an outline of a radiographic imaging system (hereinafter, referred to as an imaging system 100) of the present embodiment will be described. FIG. 1 is a block diagram illustrating the schematic configuration of the imaging system 100.

As illustrated in FIG. 1, the imaging system 100 according to the present embodiment is configured to include a control system 100a.

The control system 100a is configured to include a radiation emission apparatus (hereinafter, referred to as an irradiation apparatus 1) and one or more radiographic imaging apparatuses (hereinafter, referred to as imaging apparatuses 2).

The irradiation apparatus 1 generates radiation (such as X-rays) and emits the radiation to a subject and the imaging apparatus 2 disposed behind the subject, and is configured to include a radiation control device (hereinafter, referred to as a control device 1a) and a tube 1b. The specific configuration of the control device 1a will be described later.

The imaging apparatus 2 generates image data by receiving radiation from the irradiation apparatus 1, and can communicate with the irradiation apparatus 1. The specific configuration of the imaging apparatus 2 will also be described later.

The imaging system 100 of the present embodiment configured as described above can perform imaging of a subject by emitting radiation X from the irradiation apparatus 1 to the subject disposed between the irradiation apparatus 1 and the imaging apparatus 2.

In addition, the imaging system 100 according to the present embodiment can capture a moving image. That is, it is possible to generate a plurality of frame images forming a moving image by emitting pulsed radiation of a time width, which is set in advance, a plurality of times continuously at fixed intervals based on one imaging operation (pressing of an exposure switch (not illustrated)).

Figure 2:
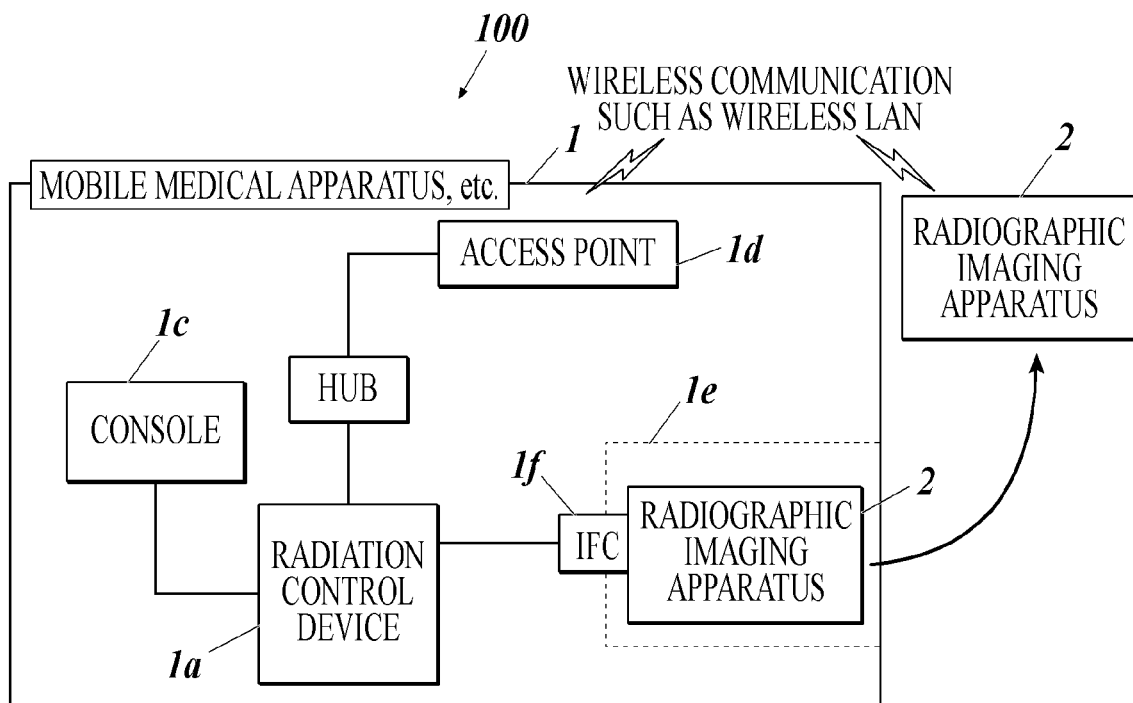
FIG. 2 is a block diagram illustrating an example of usage of the radiographic imaging system illustrated in FIG. 1.

In addition, the imaging system 100 of the present embodiment configured as described above can also be installed and used in an imaging room or the like in a hospital. For example, as illustrated in FIG. 2, a console 1c or an access point 1d, a housing 1e in which the imaging apparatus 2 is housed, a communication cable 1f for connecting the control device 1a and the imaging apparatus 2 housed in the housing 1e to each other, wheels (not illustrated), and the like are provided in the irradiation apparatus 1, thereby forming a mobile medical apparatus main body 1. A mobile medical apparatus 100 (tube 1b is not illustrated in FIG. 2) formed by combining the mobile medical apparatus main body 1 with the imaging apparatus 2 can also be used as a movable system.

In the case of performing imaging using an imaging table installed in the imaging room in the hospital, a wired cable is connected to the imaging apparatus 2 installed on the imaging table, so that transmission and reception of information between the irradiation apparatus 1 and the imaging apparatus 2, supply of electric power to the imaging apparatus 2, and the like can be performed.

For example, in the case of using a wired cable for connection with the imaging apparatus 2, it is possible to match the timings of the irradiation apparatus 1 and the imaging apparatus 2 to perform imaging by making a pulse signal or a timing signal be included in the signal of the wired cable.

However, for example, even in the imaging in the imaging room, it may be necessary to perform the imaging in a state where the subject is placed on a wheelchair or a bed. In such a case, in imaging with a wired cable attached to the imaging apparatus 2, there are the following problems.

Cable stands in the way.
There is a risk that the cable may be disconnected to cause communication failure.
There is a problem in hygiene because the cable touches the subject.

For this reason, there has been a demand for performing imaging without using a wired cable.

On the other hand, in the case of performing imaging while moving with a mobile medical apparatus, the imaging is performed in a ward where the subject is under medical treatment. In this case, imaging is performed on the bed in which the subject stays. For this reason, it is necessary to take out the imaging apparatus 2 from the housing 1e and insert the imaging apparatus 2 between the subject and the bed to perform imaging. In this case, more seriously than in the case of performing imaging in the imaging room, there are the following problems, such as a cable stands in the way, there is a risk that the cable may be disconnected to cause communication failure, and there is a problem in hygiene because the cable touches the subject. For this reason, there has been a demand for performing imaging without using a wired cable.

In particular, in imaging using known computed radiography (CR) called a flat panel detector (FPD), a wired cable is not necessary at the time of imaging. For this reason, there has been a demand for performing imaging without using a wired cable in order to obtain the same ease of operation as in the CR.

However, by using the imaging system 100 according to the present embodiment, it is possible to configure the mobile medical apparatus 100 that meets such a demand.

In addition, the imaging system 100 can be configured to be able to communicate with other systems, such as a radiology information system (RIS) and a picture archiving and communication system (PACS).

Radiation Emission Apparatus

Figure 3:
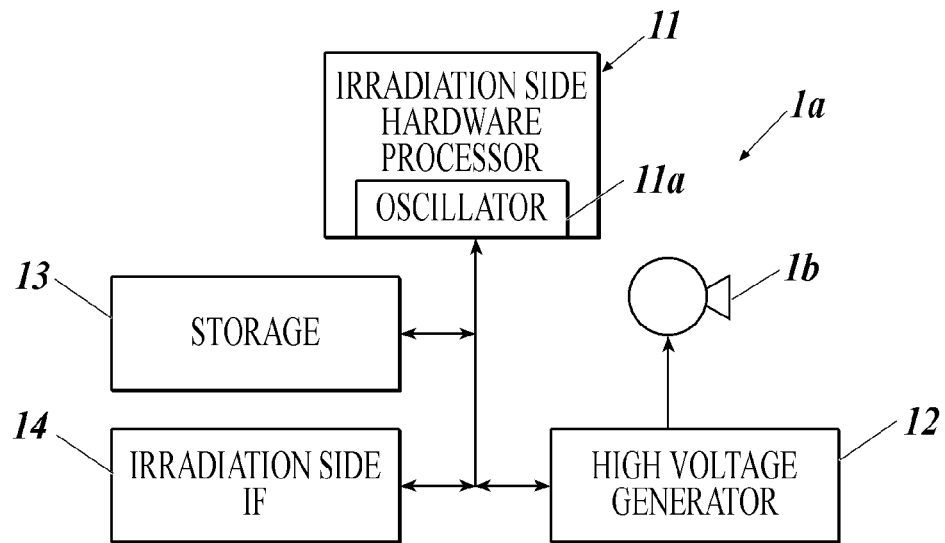
FIG. 3 is a block diagram illustrating the specific configuration of a radiation emission apparatus provided in the radiographic imaging system illustrated in FIG. 1.

Next, details of the control device 1a provided in the irradiation apparatus 1 will be described. FIG. 3 is a block diagram illustrating the specific configuration of the control device 1a.

As illustrated in FIG. 3, the control device 1a includes an irradiation side hardware processor 11, a high voltage generator 12, a storage 13, an irradiation side interface (hereinafter, referred to as an irradiation side IF 14), and the like.

In addition, each of the components 11 to 14 of the control device 1a can receive supply of electric power using a power cable or a built-in battery (not illustrated).

The irradiation side hardware processor 11 includes a CPU, a RAM, and the like, and is configured to perform overall control of the operations of the respective components 12 to 14 of the irradiation apparatus 1.

In addition, the irradiation side hardware processor 11 includes an oscillator (hereinafter, referred to as an irradiation side oscillator 11a). The irradiation side oscillator 11a can be a crystal oscillator, a ceramic oscillator, or the like that generates a clock with a predetermined cycle when the power is turned on.

Time measurement may be performed using another time measurement component other than the irradiation side oscillator 11a.

The high voltage generator 12 applies a voltage according to preset imaging conditions (for example, conditions regarding a subject, such as a part to be imaged and a physique, or conditions regarding irradiation, such as a tube voltage, a tube current, an irradiation time, and a current time product) to the tube 1b in response to the reception of the timing signal from the irradiation side hardware processor 11.

In a case where moving image capturing is included in the imaging conditions, a pulsed voltage is repeatedly applied at predetermined intervals each time a timing signal is received.

When a voltage is applied from the high voltage generator 12, the tube 1b generates radiation of a dose corresponding to the applied voltage. Specifically, when a pulsed voltage is applied from the high voltage generator 12, pulsed radiation is emitted.

The storage 13 includes a hard disk drive (HDD), a semiconductor memory, and the like, and stores various processing programs, parameters or files required to execute the processing programs, and the like.

In addition, the storage 13 can store various kinds of data (for example, time measurement information or adjustment conditions to be described later) generated in the course of the process performed by the irradiation side hardware processor 11.

The irradiation side IF 14 is configured to be able to perform at least one of transmission and reception of various kinds of information (signals or data).

Specifically, the irradiation side IF 14 is configured to include a connector for inserting the communication cable 1f, an antenna that can transmit and receive radio waves, a lamp that emits light (including infrared light) or an optical sensor that detects light, a speaker that emits sound (including ultrasonic waves) or a microphone that detects sound, a vibrator for transmitting vibration to an apparatus (imaging apparatus 2 or the like) in contact therewith or a vibration sensor for detecting vibration, a coil that generates a magnetic field, and the like.

The configuration of the irradiation side IF 14 is determined according to an information transmission method.

The irradiation side hardware processor 11 of the irradiation apparatus 1 configured as described above has the following functions according to the program stored in the storage 13.

For example, the irradiation side hardware processor 11 has a function of setting various imaging conditions (conditions regarding a subject, such as a part to be imaged and a physique or conditions regarding irradiation, such as a tube voltage, a tube current, an irradiation time, a current time product, and a frame rate).

In addition, the irradiation side hardware processor 11 generates a timing signal, which triggers application of a voltage (emission of radiation) to the high voltage generator 12, in response to the reception of a signal indicating the pressing of an exposure switch (not illustrated).

In a case where moving image capturing is included in the imaging conditions, a timing signal is repeatedly generated in a cycle corresponding to the frame rate.

Configuration of Radiographic Imaging Apparatus

Figure 4:
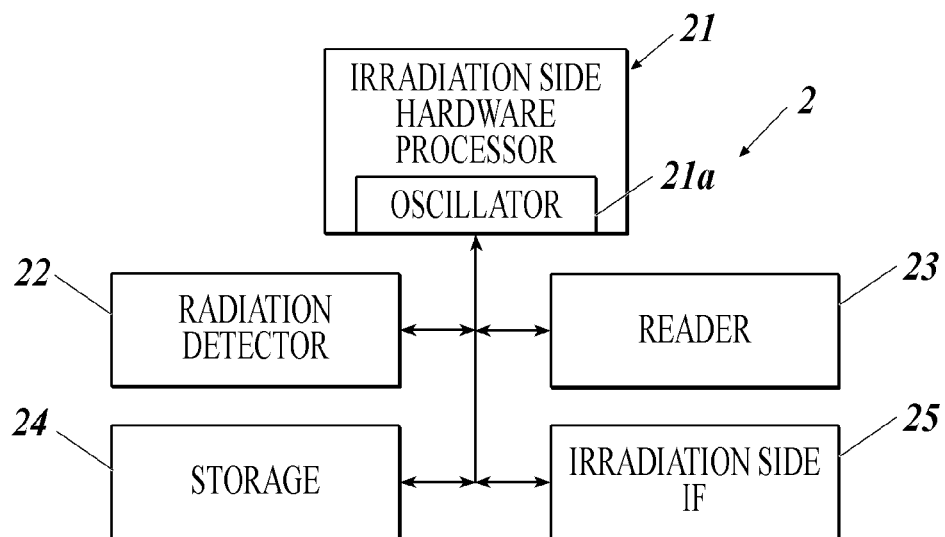
FIG. 4 is a block diagram illustrating the specific configuration of a radiographic imaging apparatus provided in the radiographic imaging system illustrated in FIG. 1.

Next, the specific configuration of the imaging apparatus 2 provided in the imaging system 100 will be described. FIG. 4 is a block diagram illustrating the specific configuration of the imaging apparatus 2.

In addition to a housing (not illustrated), the imaging apparatus 2 according to the present embodiment includes an imaging side hardware processor 21, a radiation detector 22, a reader 23, a storage 24, an imaging side interface (hereinafter, referred to as an imaging side IF 25), and the like, as illustrated in FIG. 4.

In addition, each of the components 21 to 25 of the imaging apparatus 2 can receive supply of electric power using a power cable or a built-in battery (not illustrated).

The imaging side hardware processor 21 includes a CPU, a RAM, and the like, and is configured to perform overall control of the operations of the respective components 22 to 25 of the imaging apparatus 2.

In addition, the imaging side hardware processor 21 includes an oscillator (hereinafter, referred to as an imaging side oscillator 21a). The imaging side oscillator 21a can be a crystal oscillator, a ceramic oscillator, or the like that generates a clock with a predetermined cycle when the power is turned on.

Time measurement may be performed using another time measurement component other than the imaging side oscillator 21a.

The radiation detector 22 may be any radiation detector having a substrate on which a plurality of pixels each having a radiation detection element and a switch element are arranged in a two-dimensional manner. The radiation detection element directly or indirectly generates charges whose amount corresponds to the radiation dose by receiving radiation from the outside, and the switch element is provided between each radiation detection element and a wiring line and can be switched between an ON state in which electrical connection between the radiation detection element and the wiring line can be made and an OFF state in which electrical connection between the radiation detection element and the wiring line cannot be made. A known radiation detector can be used as the radiation detector 22.

That is, the imaging apparatus 2 may be of a so-called indirect type that includes a scintillator and detects emitted light by receiving radiation with the scintillator or may be of a so-called direct type that directly detects radiation without using the scintillator or the like.

The reader 23 may be any reader configured to be able to read out the amount of charges accumulated in each of the plurality of radiation detection elements as a signal value and generate image data of a radiation image based on each signal value, and a known reader can be used as the reader 23.

The storage 24 includes a hard disk drive (HDD), a semiconductor memory, and the like, and stores various processing programs including various image processing programs, parameters or files required to execute the programs, and the like.

In addition, the storage 24 can store various kinds of data (for example, time measurement information or adjustment conditions to be described later) generated in the course of the process performed by the imaging side hardware processor 21.

The imaging side IF 25 is configured to be able to perform at least one of transmission and reception of various kinds of information (signals or data) (however, in a case where the irradiation side IF 14 performs only one of transmission and reception, at least the other).

Specifically, the imaging side IF 25 is configured to include a connector for inserting the communication cable 1f, an antenna that can transmit and receive radio waves, a lamp that emits light (including infrared light) or an optical sensor that detects light, a speaker that emits sound (including ultrasonic waves) or a microphone that detects sound, a vibrator for transmitting vibration to an apparatus (irradiation apparatus 1 or the like) in contact therewith or a vibration sensor for detecting vibration, a coil that generates a magnetic field, and the like.

The configuration of the imaging side IF 25 is determined according to the configuration of the irradiation side IF 14.

The imaging side hardware processor 21 of the imaging apparatus 2 configured as described above has the following functions according to the program stored in the storage 24.

For example, the imaging side hardware processor 21 has a function of switching the state of the imaging apparatus 2 to any one of "initialization state", "accumulation state", and "readout and transfer state".

The timing for switching the state will be described later.

The "initialization state" is a state in which an on-voltage is applied to each switch element and the charge generated by the radiation detection element is not accumulated in each pixel (charge is discharged to the signal line).

The "accumulation state" is a state in which an off-voltage is applied to each switch element and the charge generated by the radiation detection element can be accumulated in each pixel (charge is not discharged to the signal line).

The "readout and transfer state" is a state in which an on-voltage is applied to each switch element and the reader 23 is driven so that a signal value based on the charge that has flowed in can be read out.

Control System

Next, details of the control system 100a provided in the imaging system 100, which is a main part of the invention, will be described.

As described above, the control system 100a according to the present embodiment is configured by the irradiation apparatus 1 and the imaging apparatus 2.

The irradiation apparatus 1 and the imaging apparatus 2 can operate as the control system 100a by having functions listed below in addition to the radiation emission function, the charge accumulation and readout function, and the like described above.

First, the irradiation side hardware processor 11 of the irradiation apparatus 1 has a function of periodically generating time measurement information using a clock generated by the irradiation side oscillator 11a.

The time measurement information generated herein includes, for example, a timing signal or time information.

The timing signal refers to a pulsed signal that is output each time one or more clocks are generated or the like.

The time information refers to a count value of a timer that counts up in accordance with a clock or the like.

In addition, since each of the components 11 to 14 of the irradiation apparatus 1 operates based on the clock generated by the irradiation side oscillator 11a, the time measurement by the irradiation side hardware processor 11 is performed in conjunction with the irradiation apparatus 1.

In addition, the imaging side hardware processor 21 of the imaging apparatus 2 also has a function of periodically generating time measurement information using a clock generated by the imaging side oscillator 21a.

It is preferable that the format of the time measurement information generated herein matches that of the time measurement information generated by the irradiation apparatus 1.

In addition, since each of the components 21 to 25 of the imaging apparatus 2 operates based on the clock generated by the imaging side oscillator 21*a*, the time measurement by the imaging side hardware processor 21 is performed in conjunction with the imaging apparatus 2.

When the irradiation apparatus 1 is a master apparatus that is a reference of operation and the imaging apparatus 2 is a slave apparatus that follows the operation of the master apparatus, the irradiation side hardware processor 11 is a first timer, the time measurement information generated by the irradiation side hardware processor 11 is first time measurement information, the imaging side hardware processor 21 is a second timer, and the time measurement information generated by the imaging side hardware processor 21 is second time measurement information.

On the other hand, when the imaging apparatus 2 is a master apparatus and the irradiation apparatus 1 is a slave apparatus, the imaging side hardware processor 21 is a first timer, the time measurement information generated by the imaging side hardware processor 21 is first time measurement information, the irradiation side hardware processor 11 is a second timer, and the time measurement information generated by the irradiation side hardware processor 11 is second time measurement information.

Adjustment Method 1

In addition, a hardware processor of a master apparatus between the irradiation side hardware processor 11 and the imaging side hardware processor 21 has a function of transmitting the generated first time measurement information to a slave apparatus.

The function of transmitting the first time measurement information is effective when the irradiation side IF 14 of the irradiation apparatus 1 and the imaging side IF 25 of the imaging apparatus 2 are connected to each other. As a state in which the irradiation side IF 14 of the irradiation apparatus 1 and the imaging side IF 25 of the imaging apparatus 2 are connected to each other, for example, when a connector on one end side of the communication cable 1*f* is inserted into a connector of the irradiation side IF and a connector on the other end side of the communication cable 1*f* is inserted into a connector of the imaging side IF (when wired connection is made), when an antenna provided in one IF is close to an antenna in the other IF, when a lamp provided in one IF is close to an optical sensor in the other IF (including a case where connection is made by an optical cable), when a speaker in one IF is close to a microphone in the other IF, when a coil in one IF is close to a coil in the other IF, when a vibrator in one IF is in contact with a sensor in the other IF, and the like can be mentioned.

In the case of transmitting the first time measurement information by wired communication using the communication cable 1*f* that connects the irradiation apparatus 1 and the imaging apparatus 2 to each other, for example, a protocol, such as a network time protocol (NTP), or a method, such as that defined in the international standard IEEE Std. 1588-2008 (hereinafter, abbreviated as IEEE1588), can also be used.

It is preferable that a hardware processor of a slave apparatus between the irradiation side hardware processor 11 and the imaging side hardware processor 21 has a function of correcting its own second time measurement information at the time of receiving first time measurement information based on the received first time measurement information when the first time measurement information is received from a master apparatus.

In addition, at least one of the irradiation side hardware processor 11 and the imaging side hardware processor 21 has a function of storing adjustment conditions for adjusting the operation of at least one hardware processor of the irradiation side hardware processor 11 and the imaging side hardware processor 21 in the storages 13 and 24.

The "operation of the hardware processor" referred to herein refers to a timing for generating time measurement information or time measurement speed.

In addition, the "adjustment conditions" refer to the operation of the irradiation side hardware processor 11 or the imaging side hardware processor 21 for preventing the operation of the irradiation apparatus 1 and the operation of the imaging apparatus 2 from deviating from each other.

Specifically, the "adjustment conditions" are operations of the irradiation side hardware processor 11 and the imaging side hardware processor 21 for making the difference between the first time measurement information generated by the irradiation side hardware processor 11 and the second time measurement information generated by the imaging side hardware processor 21 smaller than the difference between the previously transmitted first time measurement information and the generated second time measurement information immediately after adjusting the operation of at least one hardware processor of the irradiation side hardware processor 11 and the imaging side hardware processor 21.

The adjustment conditions may be stored in advance in an apparatus at the stage of manufacture or the like, or may be stored during use of the control system 100*a*.

In addition, in the case of storing the adjustment conditions during use, it is preferable that the storage timing is other than the imaging period. As long as the storage timing is other than the imaging period, the storage timing may be a timing in a period for which the IFs 14 and 25 are connected to each other or may be a timing in a period for which the IFs 14 and 25 are disconnected from each other.

In addition, adjustment conditions calculated by another apparatus different from the control system 100*a* may be stored, or at least one hardware processor of the irradiation side hardware processor 11 and the imaging side hardware processor 21 may be made to have a function of calculating adjustment conditions and adjustment conditions calculated by the control system 100*a* may be stored.

In addition, it is preferable to store the adjustment conditions in a storage provided in an apparatus that performs adjustment between the irradiation apparatus 1 and the imaging apparatus 2.

As a method of calculating the adjustment conditions, for example, there are methods listed below.

Adjustment Conditions Calculation 1 (Calculation Based on Characteristics of Each Oscillator)

A clock for generating time measurement information is known to have a range of error that varies with the accuracy of an oscillator that generates the clock. For example, oscillators whose clock frequency is set to 10 MHz have individual differences, such as the frequency of a clock actually generated being 10.1 MHz or 9.9 MHz. If there are such individual differences between the irradiation side oscillator 11*a* and the imaging side oscillator 21*a*, the timing of generating time measurement information of the same value is shifted.

Therefore, for example, frequencies of clocks generated by the oscillators 11*a* and 21*a* are individually measured in advance, and the difference between the measured value and the set value is calculated. Then, the operation of a hardware processor that performs adjustment for making the difference small, between the hardware processors 11 and 21, is set to the adjustment conditions.

By using the method, it is possible to calculate highly accurate adjustment conditions for each of the hardware processors having the oscillators 11a and 21a.

Adjustment Conditions Calculation 2 (Calculation Based on Difference of Two Oscillators)

As described above, since there are individual differences in the accuracy of the oscillator, even if the irradiation side hardware processor 11 and the imaging side hardware processor 21 use oscillators with the same set value of the clock frequency, there is a high possibility that the timing for generating time measurement information of the same value will be shifted.

Figure 5:
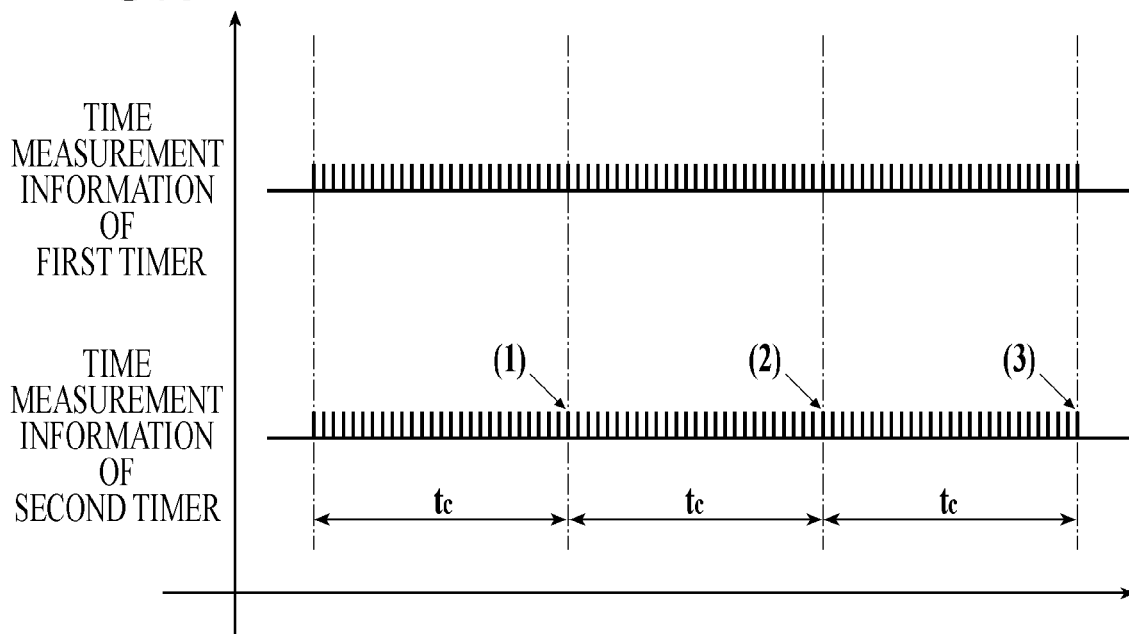
FIG. 5 is a diagram illustrating an example of a method of calculating adjustment conditions that is performed by a control system provided in the radiographic imaging system illustrated in FIG. 1.

Therefore, the clock generated by the hardware processor (first timer) of the master apparatus is continuously transmitted to the hardware processor (second timer) of the slave apparatus using the irradiation side IF 14 and the imaging side IF 25. Then, the hardware processor of the slave apparatus counts the transmitted clock of the master apparatus and the clock generated by the slave apparatus, measures the number of clocks generated by the hardware processor of the master apparatus and the number of clocks generated by the hardware processor of the slave apparatus at a timing at which a predetermined period tc has passed from the start of counting (for example, at a timing illustrated in (1) of FIG. 5), and calculates the difference therebetween. Then, the operation of a hardware processor that performs adjustment for making the difference small, between the hardware processors 11 and 21, is set to the adjustment conditions.

The predetermined period tc can be determined based on the imaging period for capturing a moving image and the difference between the clock frequencies of the respective hardware processors. Therefore, the length of the predetermined period tc may be changed for each imaging type.

In addition, at least one of the irradiation side hardware processor 11 and the imaging side hardware processor 21 has a function of adjusting the operation of at least one hardware processor of the irradiation side hardware processor 11 and the imaging side hardware processor 21 based on the stored adjustment conditions in a state where the imaging apparatus 2 does not acquire the first time measurement information.

The "state in which the imaging apparatus 2 does not acquire the first time measurement information" refers to a state in which the connection between the irradiation side IF 14 of the irradiation apparatus 1 and the imaging side IF 25 of the imaging apparatus 2 is intentionally released (for example, the communication cable 1f is disconnected from the irradiation apparatus 1 or the imaging apparatus 2) or a state in which the first time measurement information is not received due to deterioration of the communication environment or the like even though the connection between the irradiation side IF 14 and the imaging side IF 25 is not released.

As the adjustment method, for example, there are methods listed below.

Adjustment Method 1 (Thinning-Out and Addition of Timing Signals)

In a case where the first time measurement information and the second time measurement information generated by the respective hardware processors are pulsed timing signals, the above-described adjustment conditions are a signal interval and the number of signals when thinning out or adding up the timing signals.

Figure 6A:
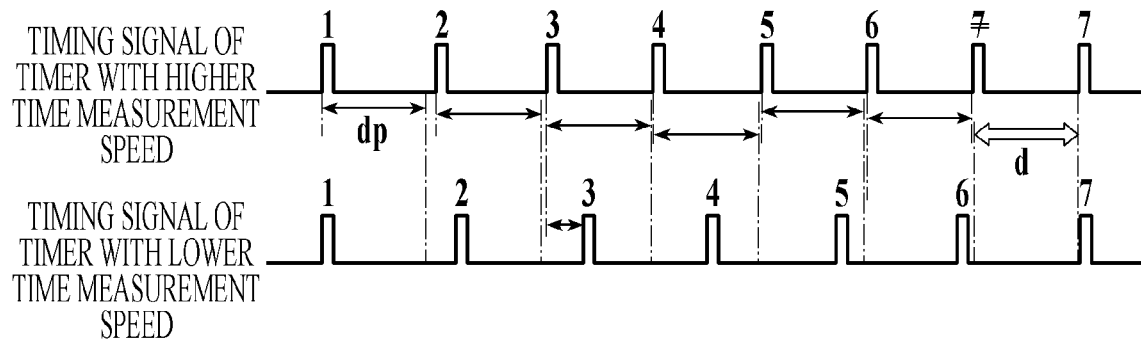
FIGS. 6A and 6B are diagrams illustrating examples of a method of adjusting the operation of a timer that is performed by the control system provided in the radiographic imaging system illustrated in FIG. 1.
Figure 6B:
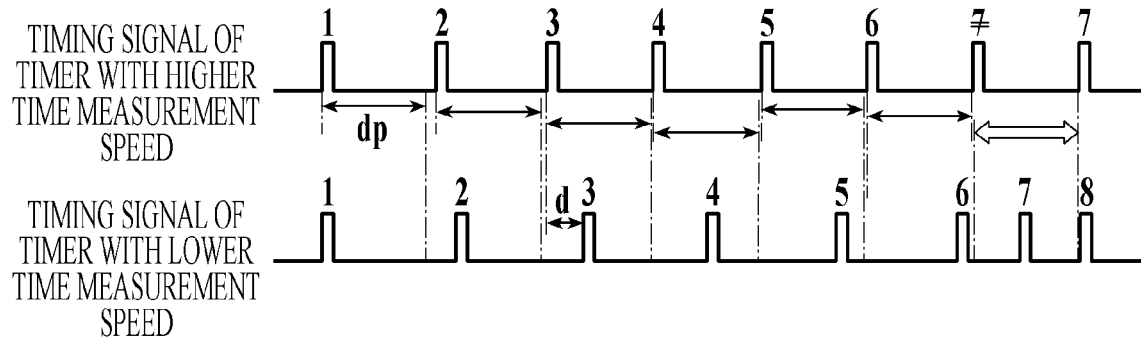

In this case, for example, as illustrated in FIG. 6A, each time a hardware processor with a higher time measurement speed between the irradiation side hardware processor 11 and the imaging side hardware processor 21 generates a predetermined number of timing signals (when a shift width d between the timing signal generated next by the hardware processor with a higher time measurement speed and the corresponding timing signal generated next by the hardware processor with a lower time measurement speed exceeds an allowable shift width dp), one or more timing signals to be generated is thinned out. Alternatively, as illustrated in FIG. 6B, each time a hardware processor with a lower time measurement speed between the irradiation side hardware processor 11 and the imaging side hardware processor 21 generates a predetermined number of timing signals, one or more new timing signals are inserted. Alternatively, both of those described above are performed.

Adjustment Method 2: Addition and Subtraction of Time Information

In a case where the first time measurement information and the second time measurement information are time information, the above-described adjustment conditions are a time adjustment amount of the time information.

In this case, the time adjustment amount is subtracted from the time measurement information generated by a hardware processor with a higher time measurement speed between the irradiation side hardware processor 11 and the imaging side hardware processor 21, the time adjustment amount is added to the time measurement information generated by a hardware processor with a lower time measurement speed between the irradiation side hardware processor 11 and the imaging side hardware processor 21, or both of these are performed (for example, an intermediate time between the first time measurement information and the second time measurement information is set).

Adjustment Method 3: Acceleration and Deceleration of Time Measurement Speed

The time measurement speed of the hardware processor can also be adjusted regardless of the form of the time measurement information. In this case, the above-described adjustment conditions are the speed adjustment amount of the time measurement speed.

Figure 7:
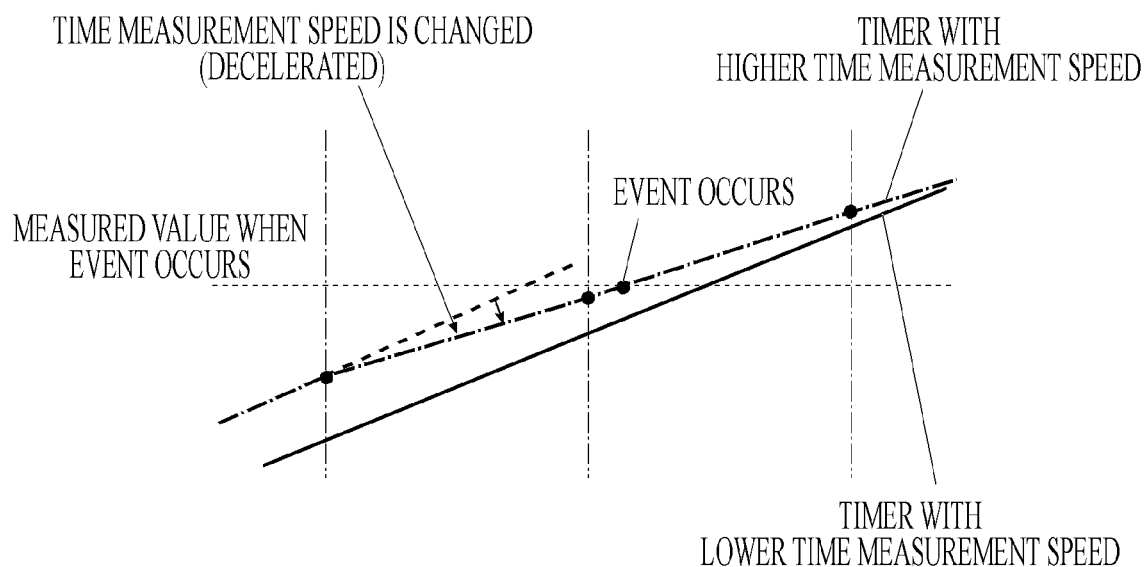
FIG. 7 is a diagram illustrating an example of a method of adjusting the operation of a timer that is performed by the control system provided in the radiographic imaging system illustrated in FIG. 1.

In this case, for example, as illustrated in FIG. 7, the time measurement speed of a hardware processor with a higher time measurement speed between the irradiation side hardware processor 11 and the imaging side hardware processor 21 is decelerated by the speed adjustment amount, or the time measurement speed of a hardware processor with a lower time measurement speed between the irradiation side hardware processor 11 and the imaging side hardware processor 21 is accelerated by the speed adjustment amount, or both of these are performed (for example, an intermediate speed between the irradiation side hardware processor 11 and the imaging side hardware processor 21 is set).

Up to now, the adjustment method of making the operation of the imaging side hardware processor 21 similar to the operation of the irradiation side hardware processor 11, or making the operation of the irradiation side hardware processor 11 similar to the operation of the imaging side hardware processor 21, or making the operation of irradiation side hardware processor 11 and the operation of the imaging side hardware processor 21 similar to each other has been described. However, for example, another time measurement component different from the irradiation side oscillator 11a and the imaging side oscillator 21a may be provided in the control system 100a, and the operation of at least one of the irradiation side hardware processor 11 and the imaging side hardware processor 21 may be made to be similar to the operation of another time measurement component.

Notification of Deviation

In addition, up to now, the case of adjusting the operation of at least one of the irradiation side hardware processor 11 and the imaging side hardware processor 21 in a case where there is a deviation between the operation of the irradiation side hardware processor 11 and the operation of the imaging side hardware processor 21 has been described. However, notification that there is a deviation may be provided without performing the adjustment.

As a notifier N for notifying that there is a deviation, a display that displays the fact that there is a deviation in the form of an image or a character, a speaker that outputs a sound indicating that there is a deviation, a vibrator that vibrates when there is a deviation, and the like can be mentioned.

Figure 8:
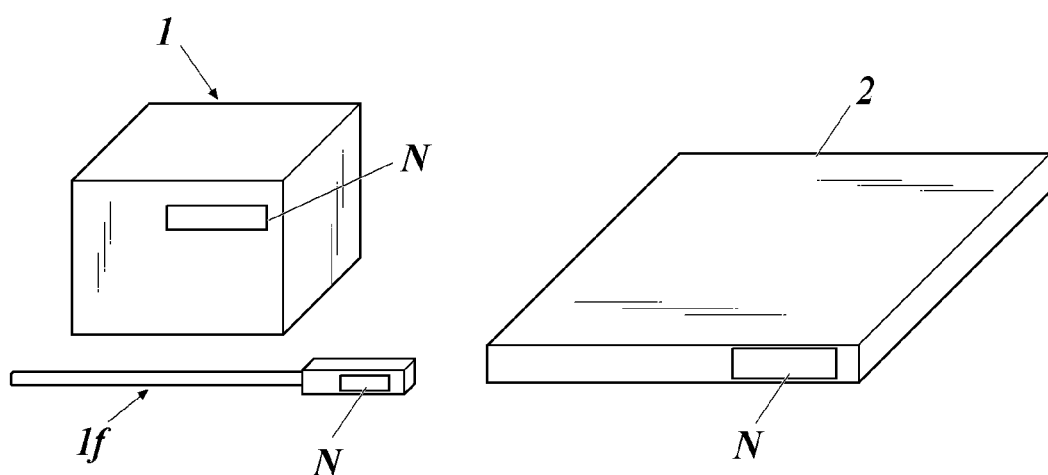
FIG. 8 is a perspective view of the control system provided in the radiographic imaging system illustrated in FIG. 1.

For example, as illustrated in FIG. 8, the notifier N may be provided at any place that can be visually recognized by the user in the control system 100a, such as the irradiation apparatus 1, the imaging apparatus 2, or the communication cable 1f.

In addition, in a case where an apparatus for detecting that there is a deviation and an apparatus for notifying that there is a deviation are different, a communicator that transmits notification content from the apparatus for detecting that there is a deviation to the apparatus for notifying that there is a deviation (for example, an antenna capable of transmitting and receiving radio waves, a lamp that emits light (including infrared light), an optical sensor that detects light, or the like) may be provided.

In this manner, the user can know that the operation timings of the irradiation apparatus 1 and the imaging apparatus 2 are shifted from each other before imaging. As a result, it is possible to prevent a situation in which imaging is performed at an incorrect timing and accordingly the subject is unnecessarily exposed.

Imaging Using Radiographic Imaging System

Figure 9:
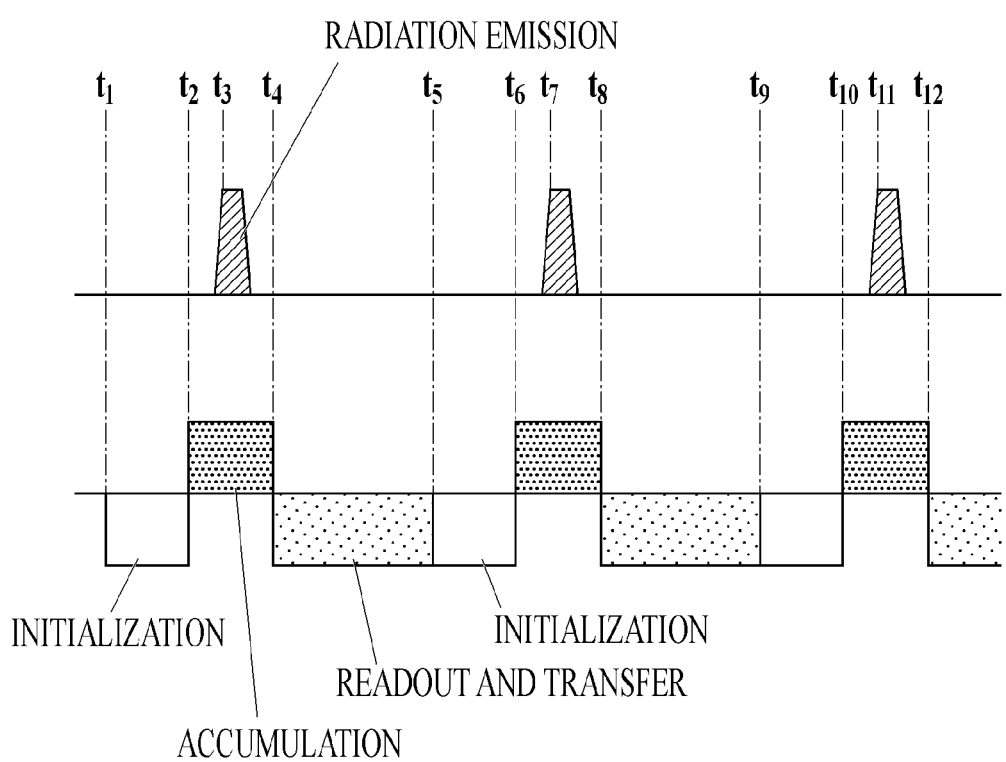
FIG. 9 is a timing chart illustrating the operation of the radiographic imaging system illustrated in FIG. 1.

Next, a basic imaging operation performed by the imaging system 100 will be described. FIG. 9 is a timing chart illustrating the operation of the imaging system 100.

Operation Start

First, the user performs an operation that triggers time measurement start by the irradiation side hardware processor 11 of the irradiation apparatus 1 and the imaging side hardware processor 21 of the imaging apparatus 2 (for example, the power of each apparatus of the imaging system 100 is turned on or the like). Then, each of the irradiation side hardware processor 11 and the imaging side hardware processor 21 starts time measurement. At this time, if the timing at which the power of each apparatus is turned on is different, the time measurement start timing of the irradiation side hardware processor 11 and the time measurement start timing of the imaging side hardware processor 21 are different. Therefore, the generation timing of time measurement information by the irradiation apparatus 1 and the generation timing of time measurement information by the imaging apparatus 2 are different at this stage.

Connection Between Irradiation Apparatus 1 and Imaging Apparatus 2

When the irradiation side IF of the irradiation apparatus 1 and the imaging side IF of the imaging apparatus 2 are connected to each other (may be connected to each other in advance), the first time measurement information is transmitted from a master apparatus between the irradiation apparatus 1 and the imaging apparatus 2 to a slave apparatus.

The slave apparatus that has received the first time measurement information corrects the operation of its own hardware processor in accordance with the operation of the hardware processor of the master apparatus (time measurement information of the same value is generated at the same timing).

Disconnection Between Irradiation Apparatus 1 and Imaging Apparatus 2

Thereafter, the user releases the connection between the irradiation side IF and the imaging side IF (moves the imaging apparatus 2 to the imaging position). Then, the slave apparatus cannot acquire the first time measurement information, and the master apparatus and the slave apparatus independently perform time measurement.

At this time, if there is an individual difference between the frequency of the clock generated by the irradiation side oscillator 11a and the frequency of the clock generated by the imaging side oscillator 21a, a deviation occurs between the operation of the irradiation side hardware processor 11 and the operation of the imaging side hardware processor 21 as time passes.

However, at least one of the irradiation side hardware processor 11 and the imaging side hardware processor 21 periodically adjusts its own operation so as to reduce the deviation. As a result, the deviation between the operation of the irradiation side hardware processor 11 and the operation of the imaging side hardware processor 21 always falls within a predetermined range and does not spread further.

In a case where the control system 100a has a function of calculating the adjustment conditions, the adjustment conditions are calculated at the timing up to this point and stored in the storage.

In this manner, at least one of the calculation of adjustment conditions, the storage of adjustment conditions, or the adjustment of the operation of the hardware processor is performed other than the imaging period (before the imaging period).

Imaging Period

Thereafter, the control system 100a controls the timing of radiation generation by the irradiation apparatus 1 and the timing of image data generation by the imaging apparatus 2 using a hardware processor provided in a master apparatus between the irradiation side hardware processor 11 and the imaging side hardware processor 21 and a hardware processor provided in a slave apparatus.

Specifically, for example, as illustrated in FIG. 9, when the second time measurement information of the imaging side hardware processor 21 becomes a first predetermined value (t1) (when the first predetermined time (t1) passes from the start of time measurement), the imaging apparatus 2 applies an on-voltage to each switch element to perform initialization for discharging the dark charge accumulated in each pixel to the signal line.

Depending on the configuration of the radiation detection element of the imaging apparatus 2, the accumulated charge may be discharged at the time of charge readout to perform an initialization operation.

Thereafter, when the time measurement information generated by the imaging side hardware processor 21 becomes a second predetermined value (t2) larger than the first predetermined value (when the second predetermined time (t2) passes from the start of time measurement), the imaging apparatus 2 applies an off-voltage to each scanning line so that the charge generated by the radiation detection element can be accumulated in the pixel. The imaging apparatus 2 continues the state in which the charge can be accumulated until the time measurement information generated by the imaging side hardware processor 21 becomes a fourth predetermined value (t4) larger than the second predetermined value (when the fourth predetermined time passes from the start of time measurement).

In addition, when the time measurement information generated by the irradiation side hardware processor 11 becomes a third predetermined value (t3) that is larger than the second predetermined value and smaller than the fourth predetermined value (when the third predetermined time passes from the start of time measurement), the irradiation apparatus 1 emits radiation to the subject and the imaging apparatus 2 behind the subject. That is, the irradiation apparatus 1 emits radiation while the imaging apparatus 2 can accumulate the charge (t2 to t4).

Then, when the imaging apparatus 2 receives the radiation, charges are generated by each radiation detection element of the radiation detector 22 and accumulated in each pixel.

In addition, when the time measurement information generated by the imaging side hardware processor 21 becomes the fourth predetermined value (t4) larger than the third predetermined value (when the fourth predetermined time (t4) passes from the start of time measurement), first, the imaging apparatus 2 applies an on-voltage to each switch element connected to each scanning line so that the charge accumulated in each pixel is discharged to each signal line in the same flow as initialization. Then, a signal value based on the charge that has flowed in is read out by the reader 23, and image data is generated based on a plurality of read signal values.

In the case of moving image capturing, the irradiation apparatus 1 and the imaging apparatus 2 repeat the above-described series of operations by the number of frame images to be captured based on the time measurement information generated by each of the irradiation apparatus 1 and the imaging apparatus 2.

Effect

However, according to the control system 100*a* according to the present embodiment, even in a state where the hardware processor of the slave apparatus does not acquire the first time measurement information, the operation of the hardware processor of at least one of the irradiation side hardware processor 11 and the imaging side hardware processor 21 is adjusted based on the stored adjustment conditions. Therefore, the difference between the timing at which the irradiation side hardware processor 11 generates time measurement information and the timing at which the imaging side hardware processor 21 generates time measurement information can be within the range that does not affect imaging.

Therefore, even if time measurement information is not transmitted from one apparatus to another apparatus during moving image capturing, it is possible to stably perform the moving image capturing.

Next, specific examples when using the imaging system 100 according to the above embodiment will be described.

EXAMPLE 1

The oscillator that generates a clock that is the basis of the time measurement information slightly changes the frequency of the generated clock depending on the use environment (temperature or the like).

In view of such an issue, calculation of adjustment conditions or adjustment of an operation may be performed before use (before start of imaging) in a state where the control system 100*a* is installed at a position when imaging is actually performed.

In this manner, the adjustment conditions can be calculated taking into consideration not only the accuracy of the oscillator but also the change in the use environment of the control system 100*a*. As a result, it is possible to calculate more accurate adjustment conditions.

EXAMPLE 2

In the imaging using the imaging system 100 according to the above embodiment, it is required to transmit and receive as much information as possible with as few (simple) operations as possible from the viewpoint of efficient imaging.

In view of such an issue, when connecting the IFs to each other to transmit the first time measurement information, information other than the first time measurement information may be transmitted and received.

Specifically, at least one hardware processor of the irradiation side hardware processor 11 and the imaging side hardware processor 21 is made to have a function of superimposing predetermined information on time measurement information to be transmitted from now on. Then, when the communication cable 1*f* is connected, predetermined information is transmitted and received using terminals other than terminals for transmitting and receiving the time measurement information among a plurality of terminals provided in the plug or the connector of the communication cable 1*f*.

In this manner, since transmission and reception of other information can be performed in parallel just by performing an operation of transmitting the time measurement information, it is possible to improve the operability of imaging.

EXAMPLE 3

Since wireless communication is relatively susceptible to environmental influences, that is, it is difficult to perform communication when the radio wave environment is poor, the user may want to use wired communication preferentially.

Figure 10:
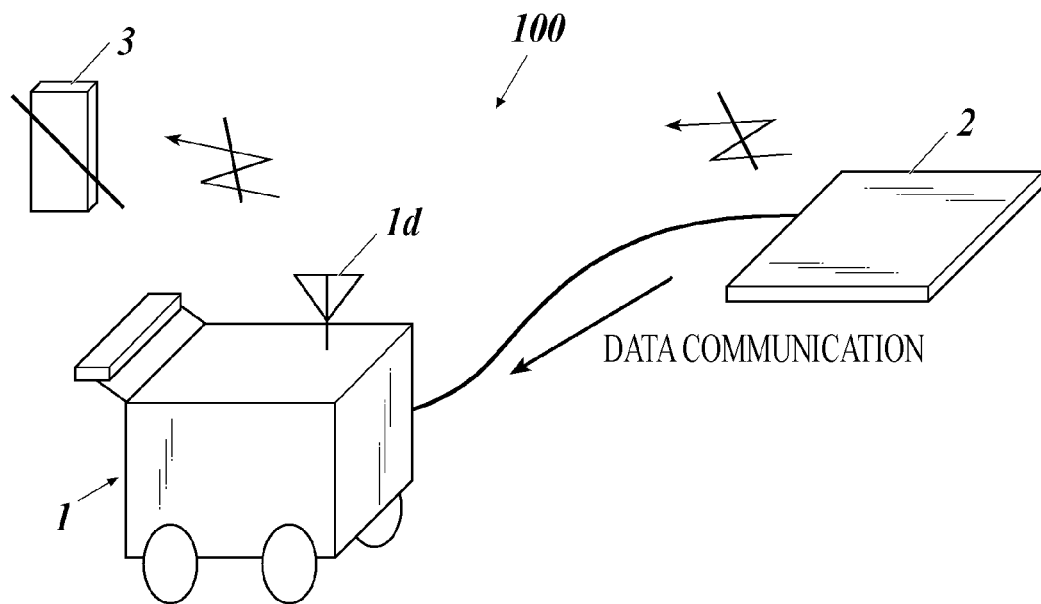
FIG. 10 is a perspective view of a radiographic imaging system according to Example 2 of the same embodiment.

For this reason, in a case where the irradiation apparatus (mobile medical apparatus main body) 1 and the imaging apparatus 2 are connected to each other wirelessly and by wire, wired communication may be preferentially used according to the radio wave environment. That is, for example, as illustrated in FIG. 10, wireless communication is disconnected, and transmission and reception of time measurement information, image data, or the like are performed by wire.

In this manner, since stable communication independent of the radio wave environment can be performed, it is possible to improve the operability of imaging.

EXAMPLE 4

Since wireless communication has many advantages in terms of handling, such as no need to connect a communication cable, the user may want to use the wireless communication preferentially.

In particular, many mobile terminals in recent years can output high-resolution images, and the data communication speed by wireless communication has also been improved. Therefore, it is required to provide such a mobile terminal 3 in the imaging system 100 and check an image with the mobile terminal 3 while charging the battery of the imaging apparatus 2 in a round visit.

Figure 11:
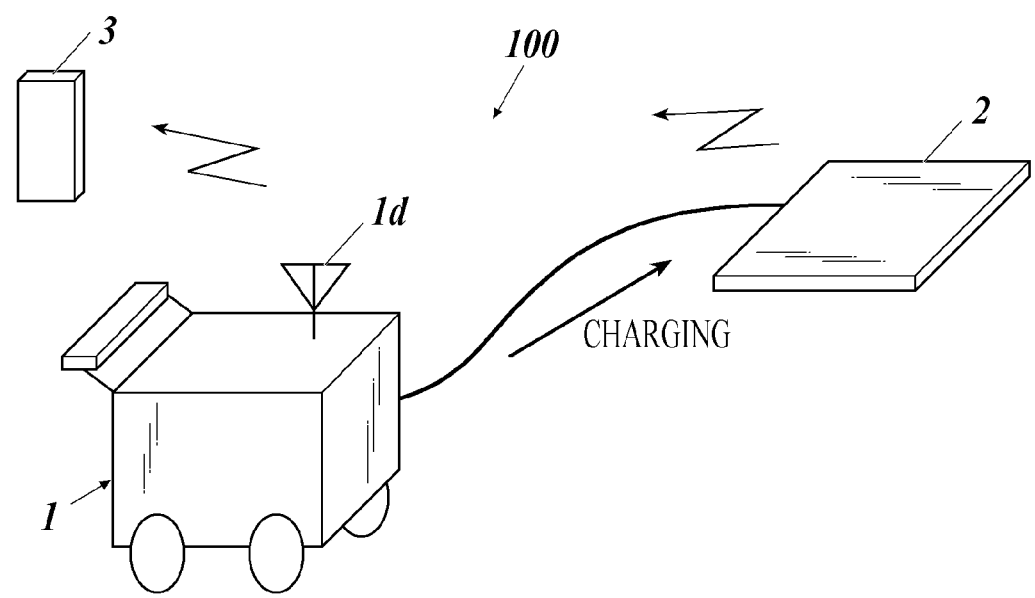
FIG. 11 is a perspective view of a radiographic imaging system according to Example 3 of the same embodiment.

For this reason, in a case where the irradiation apparatus 1 and the imaging apparatus 2 are connected to each other wirelessly and by wire, wireless communication may be preferentially used. That is, wired communication is disconnected (communication cable may remain connected), and transmission and reception of time measurement information, image data, or the like are performed wirelessly, for example, as illustrated in FIG. 11. In this case, the irradiation apparatus (mobile medical apparatus main body) 1, the imaging apparatus 2, and the mobile terminal 3 can perform wireless communication through the access point 1*d*.

In this manner, a captured image can be checked on the spot using the mobile terminal 3. Therefore, since it is not necessary to move to a monitor mounted on the mobile medical apparatus main body 1 to check the captured image every time imaging is performed, it is possible to improve the operability of imaging.

EXAMPLE 5

Assuming that the imaging system 100 according to the above embodiment has both the function of prioritizing wired communication and the function of prioritizing wireless communication that have been mentioned in the above Examples 3 and 4, means for switching to a function to be used is required.

Figure 12:
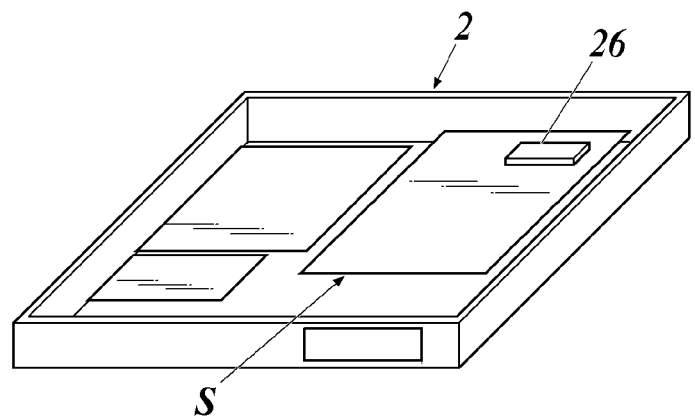
FIG. 12 is a perspective view illustrating the inside of a radiographic imaging apparatus provided in a radiographic imaging system according to Example 4 of the same embodiment.

In view of such an issue, for example, as illustrated in FIG. 12, a switch 26 for switching the function may be provided on a substrate S of a slave apparatus (the case of the imaging apparatus 2 is illustrated in FIG. 12, but the irradiation apparatus 1 may be applied) so that switching can be performed at the time of shipping or the like.

Figure 13:
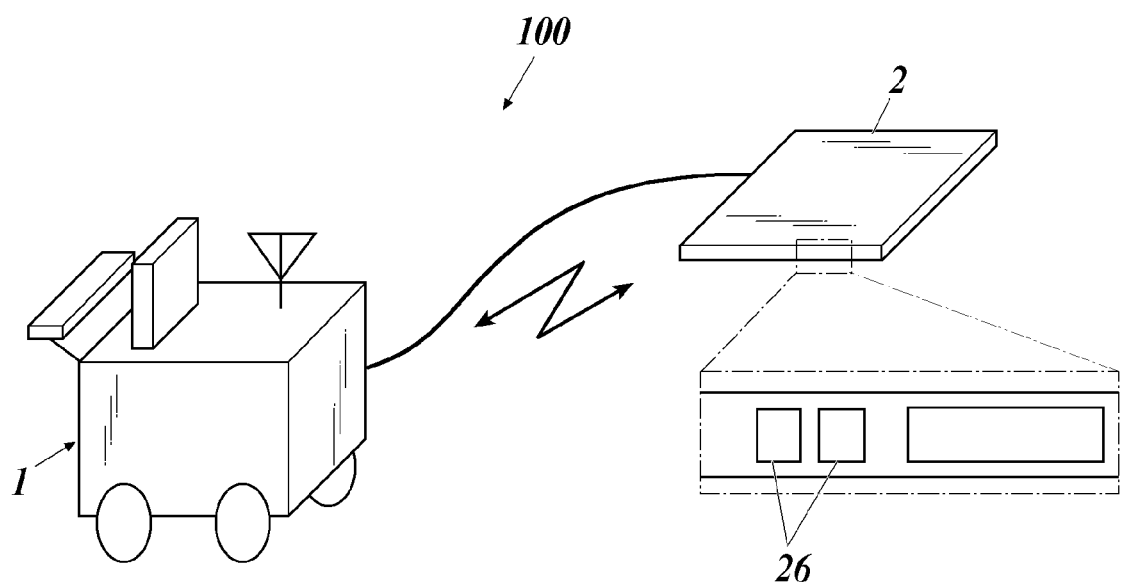
FIG. 13 is a perspective view of a radiographic imaging system according to a modification example of Example 4 of the same embodiment.

The switch 26 for switching may be provided on the surface of a slave apparatus (the case of the imaging apparatus 2 is illustrated in FIG. 13, but the irradiation apparatus 1 may be applied) so that the user can perform switching at a desired timing.

Examples of the form of the switch 26 include a button type switch that is pressed, a touch panel type switch, and a slide type switch.

In addition, the control system 100*a* may include an external apparatus (for example, a console) that can communicate with the control system 100*a*, so that switching is performed according to an instruction signal from the console.

In this manner, since switching to a function to be used between the function of prioritizing wired communication and the function of prioritizing wireless communication can be performed depending on the use case, it is possible to improve operability.

EXAMPLE 6

Figures 14A, 14B:
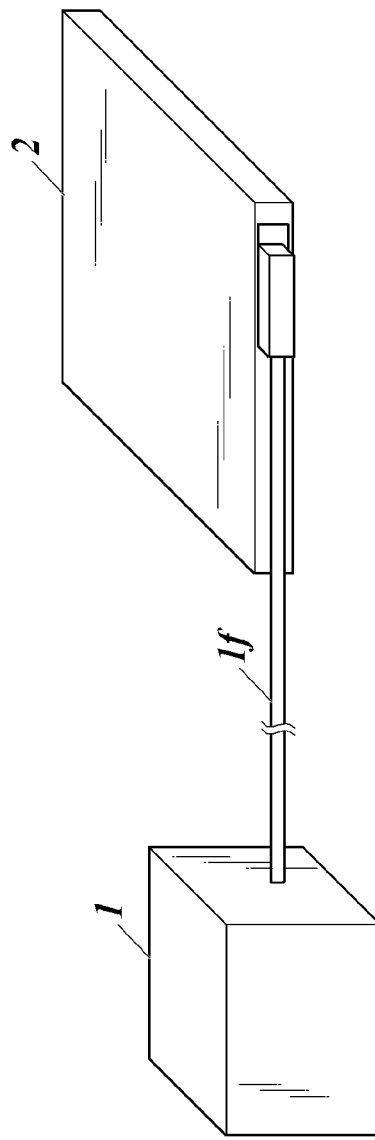
FIG. 14A is a diagram illustrating a data structure used in a radiographic imaging system according to Example 5 of the same embodiment.
FIG. 14B is a diagram illustrating the operation of the radiographic imaging system according to Example 5.

When transmitting and receiving data wirelessly or by wire, for example, as illustrated in FIG. 14A, a preamble may be added before the beginning of data.

Therefore, in the control system 100*a* according to the above embodiment, a preamble added to data may be used as the first time measurement information.

Specifically, for example, as illustrated in FIG. 14B, at least one of a hardware processor of a master apparatus and a hardware processor of a slave apparatus is made to have a function of acquiring a preamble from data, a function of correcting the second time measurement information generated by itself based on the acquired preamble, a function of calculating the adjustment conditions based on the received preamble and the generated second time measurement information, or the like.

In this manner, it is possible to correct the operation of the slave apparatus or calculate the adjustment conditions by transmitting the first time measurement information to the slave apparatus without adding a dedicated communication cable or a wireless communication method.

It can be considered that, immediately after correcting the operation of the slave apparatus using the preamble, the operation of the master apparatus and the operation of the slave apparatus will deviate from each other again due to the difference in the accuracy of the oscillators 11*a* and 21*a* provided in the master apparatus and the slave apparatus. For this reason, the operation of the slave apparatus may be corrected again using the preamble immediately before imaging (for example, when disconnecting the communication cable, or the like).

Figure 15:
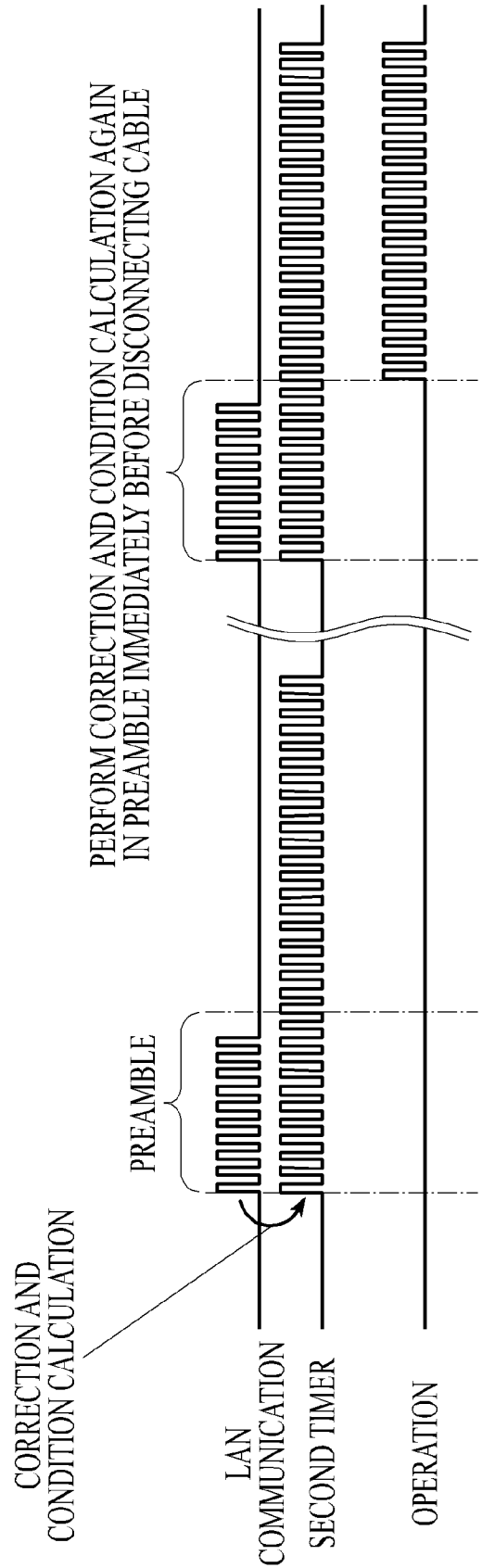
FIG. 15 is a diagram illustrating the operation of a radiographic imaging system according to a modification example of Example 5 of the same embodiment.

Specifically, for example, as illustrated in FIG. 15, the hardware processor of the master apparatus is made to have a function of retransmitting a preamble based on pressing of an exposure switch or the like.

In this manner, the operation of the slave apparatus is corrected immediately before imaging, and the operational deviation that occurs after the connection between the IFs 14 and 25 is released is also suppressed. As a result, it is possible to reliably prevent imaging in a state where the operation of the irradiation apparatus 1 and the operation of the imaging apparatus 2 deviate from each other.

EXAMPLE 7

In the imaging using the imaging system 100 described above, time measurement by a slave apparatus between the irradiation apparatus 1 and the imaging apparatus 2 after the connection between the IFs 14 and 25 is released (imaging period or the like) is performed by itself.

At this time, if there is an abnormality in the hardware processor of the slave apparatus, there is a possibility that the irradiation timing of the irradiation apparatus 1 and the charge accumulation timing on the imaging apparatus 2 side will be shifted from each other more than expected and as a result the subject will be unnecessarily exposed.

In view of such an issue, when connecting the irradiation side IF and the imaging side IF to each other, the accuracy of the operation of a hardware processor serving as a slave apparatus may be measured and compared with a set value to check whether or not there is an abnormality.

Figure 16:
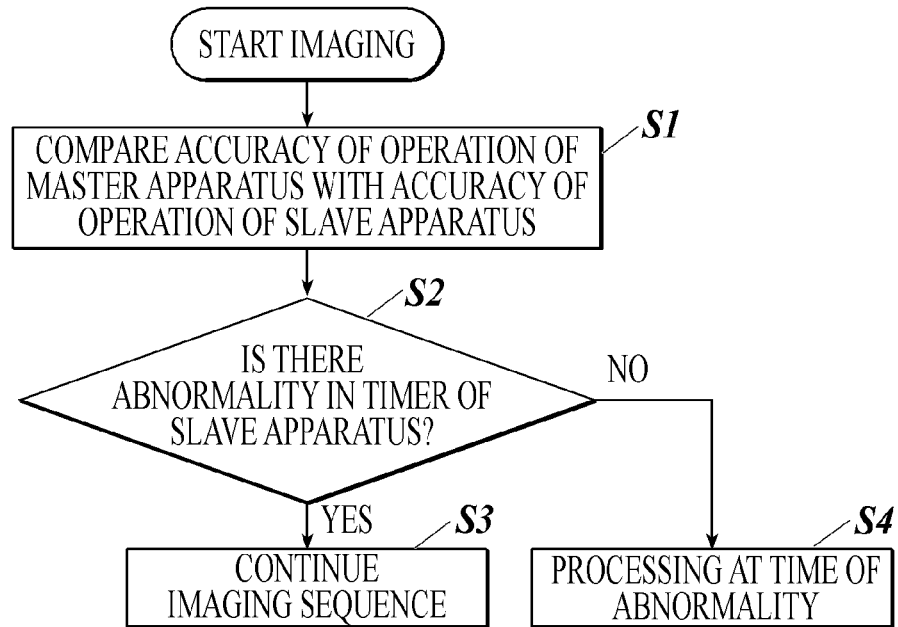
FIG. 16 is a flowchart illustrating a process performed by a radiographic imaging system according to Example 6 of the same embodiment.

Specifically, for example, as illustrated in FIG. 16, the accuracy of the operation of a master apparatus is compared with the accuracy of the operation of a slave apparatus (step S1). In a case where it is determined that there is no abnormality in the oscillator (timer) of the slave apparatus (step S2; Yes), the imaging sequence is continued (step S3). On the other hand, in a case where it is determined that there is an abnormality in the oscillator of the slave apparatus (step S2; No), processing at the time of abnormality is performed (step S4).

When checking the accuracy of the operation in step S1, the accuracy of each clock generated by the oscillators 11*a* and 21*a* may be checked, or the accuracy of the output of the time measurement information in conjunction with the oscillators 11*a* and 21*a* may be checked.

In addition, as processing at the time of abnormality in step S4, displaying that there is an abnormality, stopping of the imaging sequence, and the like can be mentioned.

In this manner, by checking the accuracy of the operation of the hardware processor serving as a slave apparatus before imaging, it is possible to check whether or not there is an abnormality in the hardware processor. As a result, it is possible to reliably prevent a situation in which imaging is performed in a state where the hardware processor is abnormal and accordingly the subject is unnecessarily exposed.

EXAMPLE 8

In addition, in view of the issue that, if there is an abnormality in the hardware processor of the slave apparatus, there is a possibility that the irradiation timing of the irradiation apparatus 1 and the charge accumulation timing on the imaging apparatus 2 side will be shifted from each other more than expected and as a result the subject will be unnecessarily exposed, the slave apparatus may include another time measurement component different from the oscillators 11a and 21a provided in the hardware processor, and the accuracy of the operation of the slave apparatus may be checked based on third time measurement information generated by another time measurement component.

Figure 17:
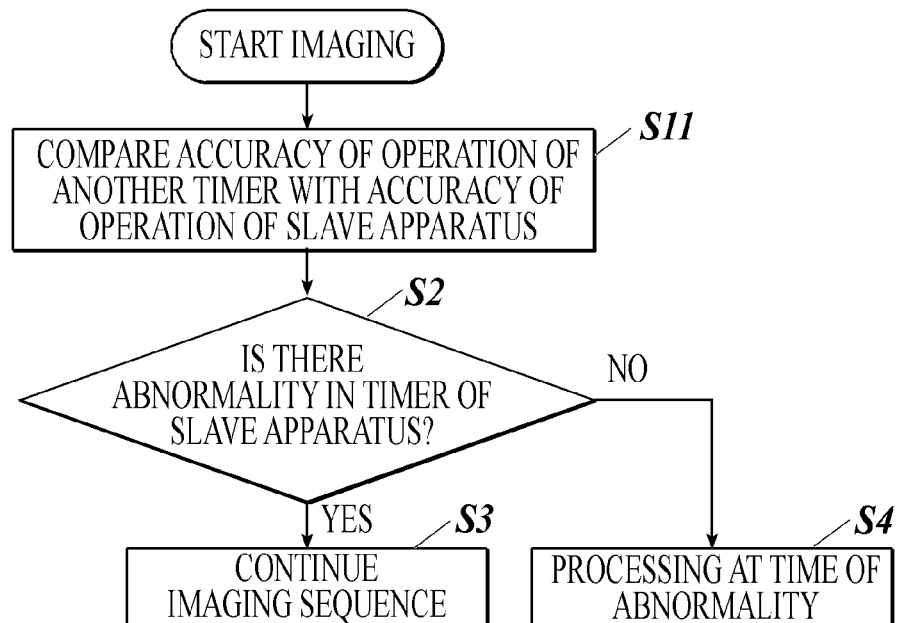
FIG. 17 is a flowchart illustrating a process performed by a radiographic imaging system according to Example 7 of the same embodiment.

Specifically, for example, as illustrated in FIG. 17, the accuracy of the operation of another time measurement component is compared with the accuracy of the operation of a slave apparatus (step S11). In a case where it is determined that there is no abnormality in the oscillator (timer) of the slave apparatus (step S2; Yes), the imaging sequence is continued (step S3). On the other hand, in a case where it is determined that there is an abnormality in the oscillator of the slave apparatus (step S2; No), processing at the time of abnormality is performed (step S4).

As the third time measurement information, for example, it is possible to use the count value of a radio controlled clock or time information defined by the NTP.

Also in this case, by checking the accuracy of the operation of the hardware processor serving as a slave apparatus before imaging, it is possible to check whether or not there is an abnormality in the hardware processor. As a result, it is possible to reliably prevent a situation in which imaging is performed in a state where the hardware processor is abnormal and accordingly the subject is unnecessarily exposed.

EXAMPLE 9

In addition, if there is an abnormality in the hardware processor of the slave apparatus, there is a possibility that the irradiation timing of the irradiation apparatus 1 and the charge accumulation timing on the imaging apparatus 2 side will be shifted from each other more than expected and as a result an incorrect image will be generated. If a diagnosis is made based on such an incorrect image, a doctor makes a wrong diagnosis.

Figure 18:
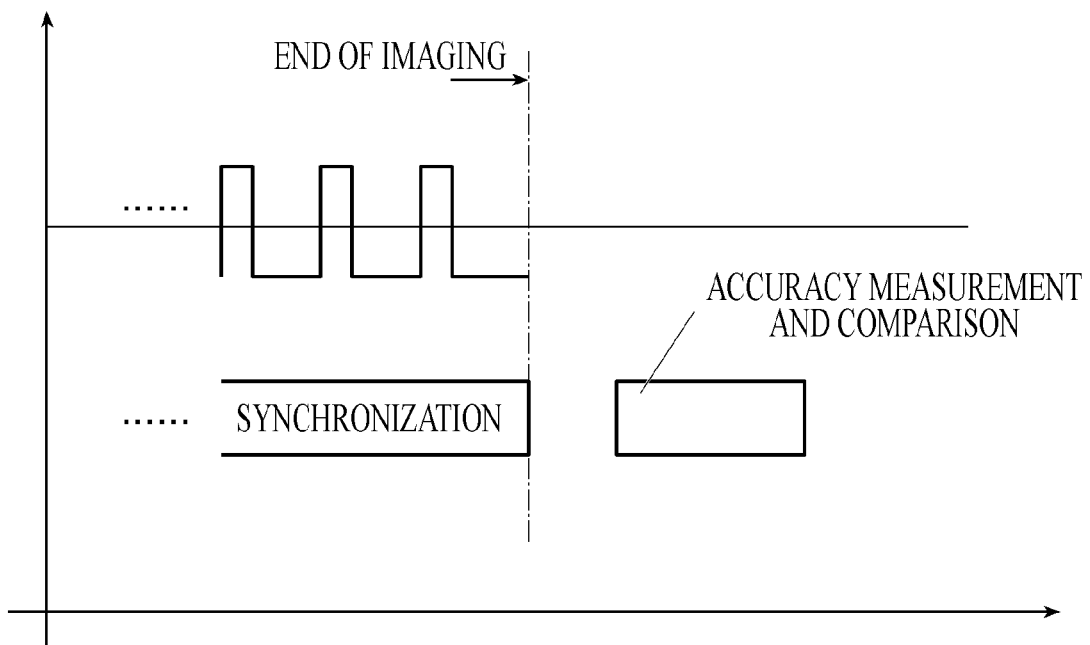
FIG. 18 is a timing chart illustrating a process performed by a radiographic imaging system according to Example 8 of the same embodiment.

In view of such an issue, for example, as illustrated in FIG. 18, after ending the imaging, the accuracy of the operation of a hardware processor serving as a slave apparatus may be measured and compared with a set value to check whether or not there is an abnormality.

In a case where there is an abnormality, the user may be notified that there is a possibility that the captured image has been captured in an abnormal state.

In this manner, by checking the accuracy of the operation of the hardware processor serving as a slave apparatus before imaging, it is possible to check whether or not there is an abnormality in the hardware processor. As a result, it is possible to reliably prevent a situation in which imaging is performed in a state where the hardware processor is abnormal and accordingly the doctor makes a wrong diagnosis.

EXAMPLE 10

Since it takes time to adjust the operation of at least one hardware processor of the irradiation side hardware processor 11 and the imaging side hardware processor 21, there is a problem that it is not possible to perform imaging even if it is desired to immediately perform imaging. However, in the field of emergency care or the like, it is important to be able to immediately perform imaging when it is desired to perform imaging. Therefore, there has been a demand for solving such a problem.

Figure 19:
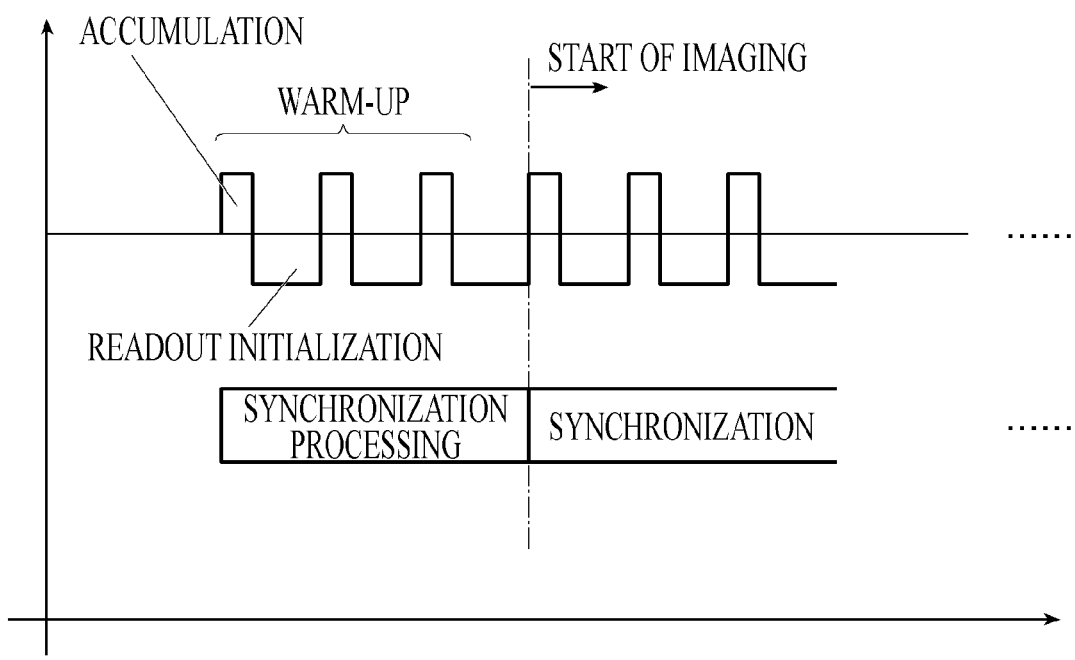
FIG. 19 is a diagram illustrating the operation of a radiographic imaging system according to Example 9 of the same embodiment.

In view of such an issue, for example, as illustrated in FIG. 19, adjustment (synchronous processing) of the operation of at least one hardware processor of the irradiation side hardware processor 11 and the imaging side hardware processor 21 may be performed during warm-up of the imaging apparatus 2 that is performed before imaging in order to stabilize a captured image.

In this manner, since the adjustment is performed in parallel with the warm-up of the imaging apparatus 2, the time until imaging becomes possible from the start of imaging preparation by the user is shortened. As a result, when the user desires to perform imaging, it is possible to perform the imaging more quickly.

EXAMPLE 11

In moving image capturing, a required frame rate changes depending on the imaging content.

On the other hand, as the frame rate increases, the number of captured images increases by the increase in the frame rate, and the amount of exposure of the subject increases. For this reason, when capturing a moving image, it is required to perform imaging at a necessary minimum frame rate according to the imaging content.

Figure 20A:
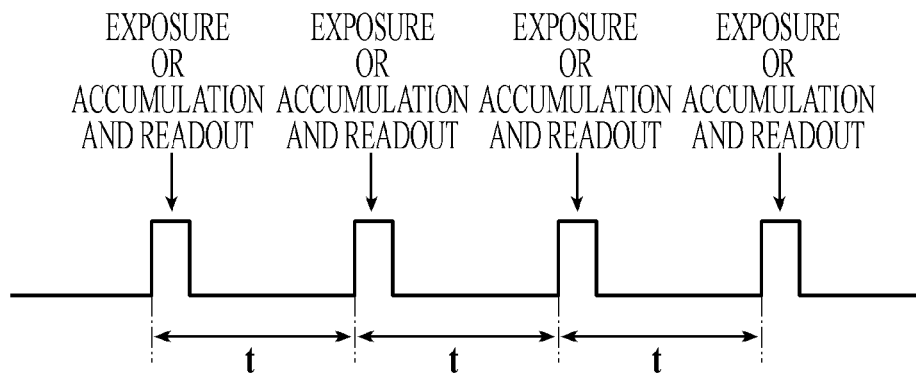
FIGS. 20A, 20B, and 20C are diagrams illustrating the operations of radiographic imaging systems according to Examples 10 and 11 of the same embodiment.
Figure 20B:
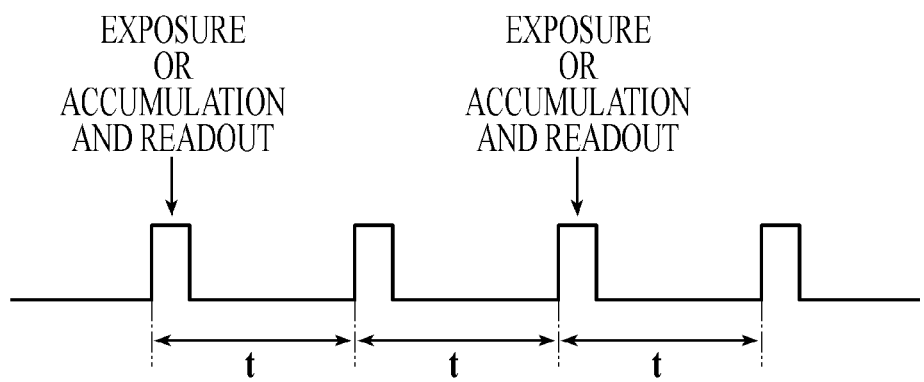

Therefore, for example, the frame rate may be changed in such a manner that the irradiation apparatus 1 and the imaging apparatus 2 generate radiation and accumulate and read out charges (skip (N−1) timing signals therebetween) each time N (=2, 3, . . . ) timing signals are generated without changing the generation cycle of the timing signal as illustrated in FIG. 20B, instead of generating the timing signal each time a predetermined time t passes and generating radiation and accumulating and reading out charges each time the timing signal is generated as illustrated in FIG. 20A.

In this manner, it is possible to suppress excessive exposure of the subject and to suppress the storage amount of captured image data.

In addition, radiation emission apparatuses or radiographic imaging apparatuses having a function of changing the frame rate generally have high performance, and many of these are expensive. However, a wide range of radiation emission apparatuses or radiographic imaging apparatuses can be made to have a function of changing the frame rate at low cost in such a manner described above.

EXAMPLE 12

Figure 20C:
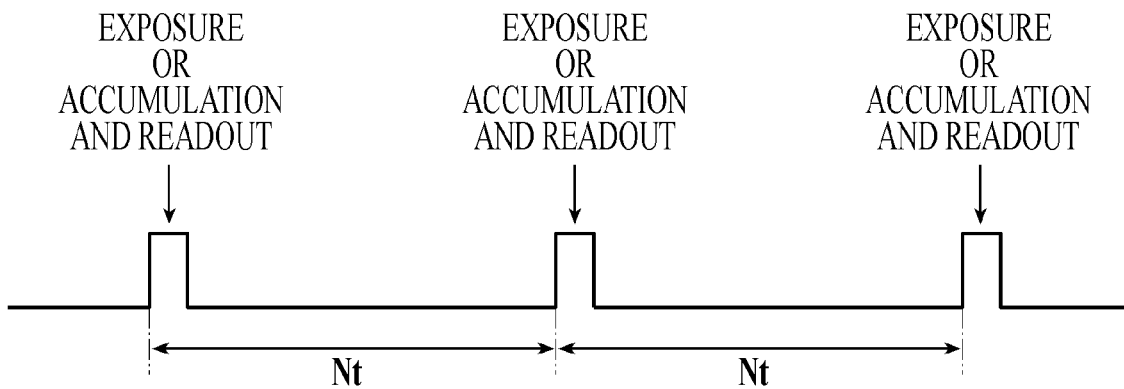

In addition, in view of the issue that it is required to perform imaging at a necessary minimum frame rate according to the imaging content when capturing a moving image, for example, the frame rate may be changed by changing the generation interval of the timing signal as illustrated in FIG. 20C, that is, in such a manner that a timing signal is generated each time N (=2, 3, . . . ) times the predetermined time t passes and the irradiation apparatus 1 and the imaging apparatus 2 operate each time the timing signal is generated, instead of the irradiation apparatus 1 or the imaging apparatus 2 operating each time N timing signals are generated as in the above Example 11.

Also in this case, it is possible to suppress excessive exposure of the subject and to suppress the storage amount of captured image data.

In addition, radiation emission apparatuses or radiographic imaging apparatuses having a function of changing the frame rate generally have high performance, and many of these are expensive. However, a wide range of radiation emission apparatuses or radiographic imaging apparatuses can be made to have a function of changing the frame rate at low cost in such a manner described above.

EXAMPLE 13

The signal used for transmission of the first time measurement information may be used alone or may be shared with other signals.

Then, in a case where the signal used for transmission of the first time measurement information is shared with other signals, several patterns can be considered for the waveform of the signal.

Figure 21A:
Figure 21B:
Figure 21C:

For this reason, it is preferable to set the waveform of the signal used to transmit the first time measurement information to, for example, a single pulse shape illustrated in FIG. 21A, an edge shape illustrated in FIG. 21B, a plurality of pulse shapes illustrated in FIG. 21C, and the like.

The signals of waveforms mentioned in FIGS. 21A to 21C can also be used as other signals. Therefore, the signals of waveforms mentioned in FIGS. 21A to 21C can be applied to various systems.

In addition, since the circuit for transmitting and receiving other signals can be used for transmission and reception of the first time measurement information, it is not necessary to provide a dedicated circuit for transmitting and receiving the first time measurement information. As a result, it is possible to suppress the manufacturing cost, size, and the like of the apparatus.

EXAMPLE 14

In a case where the first time measurement information is transmitted in the form of signals of the waveforms (single pulse type, edge detection type, and multiple pulse type) mentioned in Example 13, a wiring line should be used for that purpose. For this reason, there has been a case where a dedicated line is required. In particular, in the case of using a wiring line based on a standard widely spread such as a LAN cable, there is a problem that the wiring line becomes insufficient.

Figure 21D:

In view of such a problem, the first time measurement information may be transmitted in the form of a command illustrated in FIG. 21D using a wiring line for transmitting and receiving a command.

Figure 22:
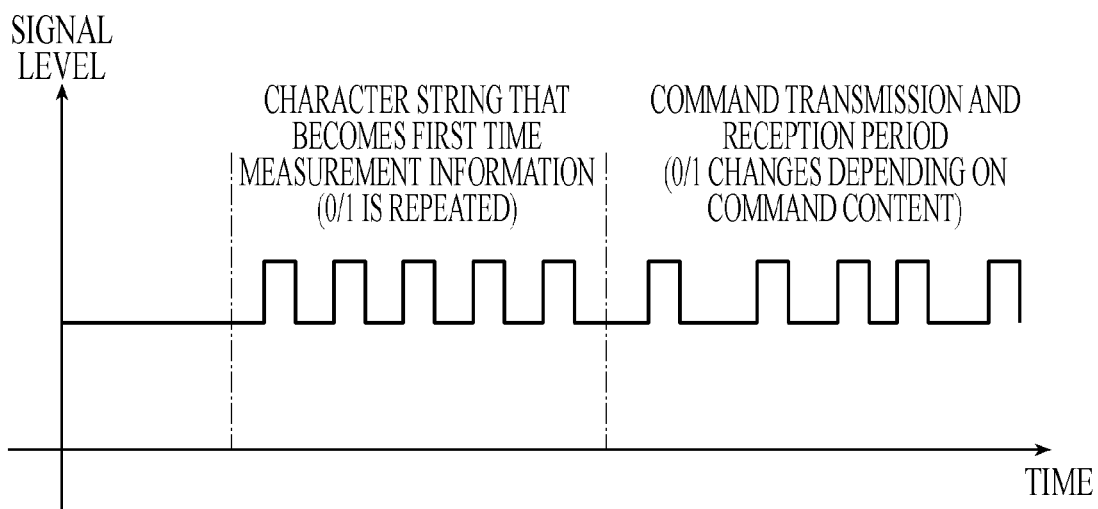
FIG. 22 is a diagram illustrating the operation of a radiographic imaging system according to Example 13 of the same embodiment.

In this case, for example, as illustrated in FIG. 22, a character string (for example, a character string in which 0 and 1 are repeated) that can be used as the first time measurement information when converted into a signal may be added to the command and transmitted as a part of the command, or a period for transmitting the first time measurement information at a timing different from command transmission and reception may be set and a character string that can be used as the first time measurement information may be transmitted and received.

In this manner, since a dedicated line for transmitting the first time measurement information is not necessary, the number of wiring lines between the irradiation apparatus 1 and the imaging apparatus 2 can be reduced.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-129641, filed on Jul. 9, 2018, is incorporated herein by reference in its entirety.

What is claimed is:

1. A control system, comprising:
   a radiation emission apparatus that generates radiation; and
   a radiographic imaging apparatus that generates image data by receiving radiation,
   wherein
   a first apparatus of the radiation emission apparatus and the radiographic imaging apparatus includes a first timer that performs time measurement in conjunction with the first apparatus to periodically generate first time measurement information,
   a second apparatus of the radiation emission apparatus and the radiographic imaging apparatus includes a second timer that performs time measurement in conjunction with the second apparatus to periodically generate second time measurement information,
   the first apparatus includes an interface that transmits the first time measurement information generated by the first timer to the second timer of the second apparatus, and
   at least one apparatus of the radiation emission apparatus and the radiographic imaging apparatus comprises:
      a storage that stores adjustment conditions for adjusting an operation of the first or second timer provided in the at least one apparatus; and
      a hardware processor that adjusts the operation of the first or second timer provided in the at least one apparatus based on the stored adjustment conditions in a state where the second timer does not acquire the first time measurement information.

2. The control system according to claim 1, wherein the hardware processor calculates the adjustment conditions.

3. The control system according to claim 2, wherein
   immediately after adjusting the operation of the first or second timer provided in the at least one apparatus comprising the hardware processor, the hardware processor calculates, as the adjustment conditions, operations of the first timer and the second timer for making a difference between the first time measurement information generated by the first timer and the second time measurement information generated by the second timer smaller than a difference between the transmitted first time measurement information and the generated second time measurement information, and
   the storage stores the calculated adjustment conditions.

4. The control system according to claim 3, wherein
   the first time measurement information and the second time measurement information are pulsed timing signals, the adjustment conditions are a signal interval and a number of signals when thinning out or adding up the timing signals, and (i) a hardware processor of an apparatus including a timer with a higher time measurement speed between the first timer and the second timer thins out at least one timing signal to be generated each time the timer with the higher time measurement speed generates a predetermined number of timing signals, or (ii) a hardware processor of an apparatus including a timer with a lower time measurement speed between the first timer and the second timer inserts at least one new timing signal each time the timer with the lower time measurement speed generates a predetermined number of timing signals, or (iii) both of (i) and (ii) are performed.

5. The control system according to claim 3, wherein
the first time measurement information and the second time measurement information are time information,
the adjustment conditions are a time adjustment amount of the time information, and (i) a hardware processor of an apparatus including a timer with a higher time measurement speed between the first timer and the second timer subtracts the time adjustment amount from time measurement information generated by the timer with the higher time measurement speed, or (ii) a hardware processor of an apparatus including a timer with a lower time measurement speed between the first timer and the second timer adds the time adjustment amount to time measurement information generated by the timer with the lower time measurement speed, or (iii) both of (i) and (ii) are performed.

6. The control system according to claim 3, wherein
the adjustment conditions are a speed adjustment amount of time measurement speed, and (i) a hardware processor of an apparatus including a timer with a higher time measurement speed between the first timer and the second timer reduces the time measurement speed of the timer with the higher time measurement speed by the speed adjustment amount, or (ii) a hardware processor of an apparatus including a timer with a lower time measurement speed between the first timer and the second timer increases the time measurement speed of the timer with the lower time measurement speed by the speed adjustment amount, or (iii) both of (i) and (ii) are performed.

7. The control system according to claim 1, wherein, other than an imaging period, the hardware processor performs at least one of calculation of the adjustment conditions, storage of the adjustment conditions by the storage, and adjustment by the hardware processor.

8. The control system according to claim 7, wherein, before the imaging period, the hardware processor performs at least one of calculation of the adjustment conditions, storage of the adjustment conditions in the storage, and adjustment by the hardware processor.

9. The control system according to claim 1, wherein
the interface transmits the first time measurement information by wired communication using a communication cable that connects the radiation emission apparatus and the radiographic imaging apparatus to each other, and
by removing the communication cable from the radiation emission apparatus or the radiographic imaging apparatus, the second timer does not acquire the first time measurement information.

10. The control system according to claim 1, wherein a timing of radiation generation by the radiation emission apparatus and a timing of image data generation by the radiographic imaging apparatus are respectively controlled by using the first timer and the second timer.

11. A radiographic imaging system comprising the control system according to claim 1.

* * * * *